(12) United States Patent
Sprague

(10) Patent No.: US 6,274,005 B1
(45) Date of Patent: Aug. 14, 2001

(54) METHOD FOR THE PREPARATION OF HEXAFLUOROACETONE

(75) Inventor: Lee G. Sprague, Augusta, GA (US)

(73) Assignee: Halocarbon Products Corporation, River Edge, NJ (US)

( * ) Notice: Subject to any disclaimer, the term of this patent is extended or adjusted under 35 U.S.C. 154(b) by 0 days.

(21) Appl. No.: 09/579,196

(22) Filed: May 26, 2000

(51) Int. Cl.[7] ................................... C07C 45/00
(52) U.S. Cl. ...................................... 204/157.93
(58) Field of Search ......................... 204/157.93

(56) References Cited

U.S. PATENT DOCUMENTS 4,885,398 * 12/1989 Sonoi et al. .................. 568/404

FOREIGN PATENT DOCUMENTS

61277645 * 12/1986 (JP) .

* cited by examiner

Primary Examiner—Edna Wong
(74) Attorney, Agent, or Firm—Norris McLaughlin & Marcus

(57) ABSTRACT

A process for preparing hexafluoroacetone comprising the reaction of 2-chloro-1,1,1,3,3,3-hexafluoropropane [R226da] with oxygen in the presence of actinic light.

12 Claims, No Drawings

METHOD FOR THE PREPARATION OF HEXAFLUOROACETONE

BACKGROUND OF THE INVENTION

1. Field of the Invention

The present invention relates to hexafluoroacetone and a method of preparation for same.

2. Description of Related Art

Many organic compounds which are polyfluorinated or perfluorinated are quite valuable. Some of the many uses of one such simple perfluorinated ketone, hexafluoroacetone [HFA], were reviewed a number of years ago. The varied uses include polymeric monomers or intermediates for monomers as well as solvents, chemicals and drug products such as sevoflurane. However, the commercial availability of HFA is limited to only trivial amounts.

There are several reactions available which allow one to prepare HFA. Bigelow first described the direct reaction of acetone with elemental fluorine. The efforts of others to control the extreme reactivity of this reaction were partially successful, but the cost of elemental fluorine is too high to be economically viable.

The halogen exchange reaction of hexachloroacetone with hydrogen fluoride [HF] has been described in French Pat. 1,372,549, with other variations following. The reaction is performed in the vapor phase over a suitable catalyst. The preferred catalyst consists of a trivalent chromium compound. This reaction suffers from the high boiling point of hexachloroacetone which makes it hard to vaporize at industrially preferred pressures of 100 to 250 psig. Also conversion is not complete and toxic chlorofluoroacetone by-products are produced. Great care must be taken to remove these completely from the product. Finally, the product is isolated as a fluorohydrin, a compound formed from the ketone and hydrogen fluoride rather than in the ketone itself. The HFA fluorohydrin is an adduct which is sufficiently stable so that it can be distilled without decomposition. Hydrogen fluoride can be removed by supercritical distillation process. Alternatively, hydrogen fluoride can be removed by scrubbing with sodium fluoride, sulfur trioxide or $NaBO_2$. All of these steps make the fluorohydrin undesirable as an intermediate in the ketone manufacture.

Suitable fluoro-olefins can be oxidized to yield HFA. U.S. Pat. No. 2,617,836 teaches the use of perfluoroisobutylene, a by-product from the production of hexafluoropropylene. However, perfluoroisobutylene's extreme toxicity precludes its shipment and handling. The oxidation of hexafluoropropylene is taught by Carlson in U.S. Pat. No. 3,536,733 to yield interalia HFA. The similar boiling points of the product, unreacted starting material and by-products which include hexafluoropropylene oxide and pentafluoropropionyl fluoride make separation tedious.

Once purified, hexafluoropropylene oxide can be isomerized to HFA, as in U.S. Pat. No. 3,213,134 with a catalyst of antimony pentafluoride. The added separations and isomerization make this preparation less convenient.

Oxidation of hexafluorothioacetone dimer is illustrated by Middleton as a convenient preparation of HFA, but the dithiane must first be prepared from hexafluoropropylene and thus adds another step to the process and additional waste in the form of sulfite/sulfate.

Direct oxidation of highly fluorinated hydrocarbons with oxygen and chlorine as initiator has been described by Haszeldine. The products are straight chain acyl halides or acids of the corresponding fluorinated hydrocarbon. Ketones were not obtained as products. A suitable hydrofluoropropane for direct oxidation to HFA would be 1,1,1,3,3,3-hexafluoropropane, R236fa. High temperature reactions of R236fa in the range of 550–585° C. have been previously described by McBee. However, the paucity of reported detail masks the fact that poor conversions are a result of poor reactivity. Thus, a highly reactive initiator such as elemental fluorine is required to oxidize R236fa directly to HFA, as illustrated in U.S. Pat. No. 5,629,460.

A disadvantage of the above fluorine initiated direct oxidation is that water is produced as a by-product. Water combines with HFA to form a hydrate, sesquihydrate and trihydrate, depending on the amount of water present. These hydrates are stable and may be sublimed or distilled without liberation of anhydrous HFA. Water must be removed from these hydrates by use of a water sequestering agent such as $P_2O_5$ or $SO_3$.

Thus, what is needed is a means to prepare HFA on an industrial scale from materials that are readily available, of low toxicity and easily handled. The reaction should give high conversion and yield in one step and be largely free of by-products that produce stable adducts or make separation difficult.

SUMMARY OF THE INVENTION

The foregoing objects were achieved with the present invention, which relates in general to a process for the preparation of hexafluoroacetone which comprises the reaction of 2-chloro-1,1,1,3,3,3-hexafluoropropane [R226da] with oxygen in the presence of actinic light.

DETAILED DESCRIPTION OF THE INVENTION

The present invention provides a means to produce HFA in high conversions and yields by the reaction of 2-chloro-1,1,1,3,3,3-hexafluoropropane [R226da] with oxygen. The reaction can be initiated by actinic light and can be conducted in either the liquid phase or the vapor phase, in a continuous manner or as a batch reaction. Reagents which accelerate the reaction such as chlorine or fluorine etc. may be added, but that is not necessary in the presence of light.

Temperature and pressure are not critical, so the invention may be practiced at any practical temperature or pressure. Temperatures may be between about 75 and 200° C. but the preferred zone is about 85 to 150° C. The pressure may vary from subatmospheric to 500 psig; the preferred range is about 100 to 250 psig; most preferably from about 125 to 200 psig.

R226da can be made from either the hydrogenation of 2,2-dichlorohexafluoropropane or from the reaction of HF and a variety of hydrochloropropanes or chloropropenes. These reactions are outlined in part in U.S. Pat. No. 5,902,911 and PCT International Application WO 99/40053 respectively.

Another aspect of the invention is that the reaction is conducted in the presence of actinic light. Wavelengths in the ultraviolet region are especially effective and the preferred illumination is from a mercury arc lamp, which provides light of 254 nm wavelength. The outcome of the reaction is remarkable in that HFA is photochemically unstable at these wavelengths, yielding inter alia hexafluoroethane. It is not possible to presuppose that although the reaction of R226da with oxygen produces HFA that this product could be isolated in good yield. It was possible that the HFA thus formed might have decomposed at a faster rate and that most or all of the reaction products would have resulted from decomposition. In the present invention this is not the case.

The reaction of R226da with oxygen progresses in the presence of actinic light without the need of added initiators or catalysts. Alternatively, the rate of reaction may be increased by the addition of selected compounds, which act as catalysts or accelerators. Examples are chlorine, fluorine or other species capable of hydrogen atom abstraction. Under the reaction conditions atomic chlorine is photochemically generated and so this accelerator is made in situ. The use of other catalytic compounds may be affected by their continuous addition during the reaction to increase the rate.

Products of the reaction and any unconverted starting material may be isolated by any suitable means, but distillation is preferred. An advantage of the present invention over U.S. Pat. No. 5,629,460 which uses R236fa is that the by-product is principally HCl, not water or HF. HCl is the preferable by-product as HFA and HCl do not form a thermally stable adduct and mixtures of the two may be readily distilled from one another. By comparison, HFA cannot be distilled from hydrated mixtures without the benefit of a water sequestering agent such as $SO_3$, $P_2O_5$ or $MgSO_4$. Distillation from mixtures of HF requires sodium fluoride scrubber beds or supercritical distillation techniques.

An additional aspect of the invention is that it is well suited to continuous operation. The R226da and oxygen reagents may be continuously metered into a reactor as vapor. This may be accomplished, for example, by heating the R226da to a temperature of 78 to 113° C., sufficient to generate a vapor pressure of the R226da which is 10 to 20 psig above the operating pressure of a downstream distillation column. The preferred reaction pressures are between 100 psig and 250 psig. The preferred reaction temperatures are those above the dew point of the reaction mixture, but as a matter of practice are limited to not more than 150° C.

After removal of the by-product HCl, the remaining reaction mixture may be further fractionated by distillation. The product HFA, unreacted R226da and any hydrates of HFA may be separated and the recovered R226da recycled through the reactor with more oxygen.

The amount of oxygen that is mixed with the R226da may be experimentally varied by methods not requiring special skill in the art to determine the optimum amount for the reaction conditions. Substoichiometric amounts of oxygen will produce higher yields of HFA but with lower conversions of R226da. Superstoichiometric amounts and unreacted oxygen are wasteful and lead to losses of product with the excess oxygen vapor.

Without further elaboration, it is believed that one skilled in the art can, using the description herein, utilize the present invention to its fullest extent. The following examples are to be construed as illustrative, and not as constraining the remainder of the disclosure in any way whatsoever.

EXAMPLES

The described process can be run in high yields and both reaction products are commercially useful. The reaction can be run either as a batch process or in a continuous manner as the following examples illustrate. The products and starting materials were separated using conventional means. The analyses were performed using gas chromatography.

Example 1

The batch oxidation was performed in a 9 gallon reactor equipped with a quartz light well, an agitator and various valves required to add and remove materials. The reaction was begun by evacuating the reactor and preheating it to 85° C. Oxygen as added to 7½ psia and R226da was added to 15 psia. The mixture was illuminated with a 450 W medium pressure mercury lamp. Reaction progress was monitored by gas chromatography and is summarized in Table 1.

TABLE 1

| Batch Oxidation of R226da | | | | |
|---|---|---|---|---|
| Reaction Time | 0 minutes | 15 minutes | 30 minutes | 45 minutes |
| Temperature | 88.2 ° C. | 110.5 ° C. | 119.3 ° C. | 118.9 ° C. |
| Pressure | 15 psia | 17 psia | 18 psia | 18¼ psia |
| HFA | — | 17.1% | 48.3% | 88.3% |
| R216aa | 1.4% | 3.1% | 4.9% | 10.7% |
| R226da | 97.2% | 76.9% | 44.6% | <0.1% |
| others | 1.4% | 2.9% | 2.2% | 1.0% |

Example 2

The reactor described in example one was held at constant 165 psia pressure while R226da (5.96 lbs, 32.0 moles) and oxygen (1.02 lbs, 31.9 moles) were continously fed over 405 minutes. Samples were withdrawn at 65, 110, 195, 270 and 330 minutes and had approximately the same composition by GC/MS analysis: 9.4% $O_2$, 28.7% R226da, 28.3% HFA, 10.1% HFA hydrate and 23.5% others. This represents mass balance of 98%, conversion of 62% and yield of HFA and hydrates of 62%.

It will be understood that the specification and examples are illustrative but not limitative of the present invention and that other embodiments within the spirit and scope of the invention will suggest themselves to those skilled in the art.

What is claimed is:

1. A process for preparing hexafluoroacetone, said process comprising the reaction of 2-chloro-1,1,1,3,3,3-hexafluoropropane [R226da] with oxygen in the presence of actinic light.

2. The process according to claim 1, which is conducted in the presence of a reagent which accelerates the reaction of 2-chloro-1,1,1,3,3,3-hexafluoropropane [R266da] with oxygen.

3. The process according to claim 2, wherein the reagent which accelerates the reaction of 2-chloro-1,1,1,3,3,3-hexafluoropropane [R226da] with oxygen is selected from the group consisting of fluorine, chlorine and other compounds which are capable of abstracting hydrogen.

4. The process according to claim 1, which is conducted at a pressure ranging from subatmospheric to 500 psig.

5. The process according to claim 4, which is conducted at a pressure ranging from 100–250 psig.

6. The process according to claim 1, which is conducted at a pressure ranging from 125–200 psig.

7. The process according to claim 1, which is conducted at a temperature ranging from 75–200° C.

8. The process according to claim 1, which is conducted at a temperature ranging from 85–150° C.

9. The process according to claim 1, which is operated as a continuous process.

10. The process according to claim 1, which is operated as a batch process.

11. The process according to claim 1, which is conducted as a vapor phase process.

12. The process according to claim 1, which is conducted as a liquid phase process.

* * * * *